United States Patent [19]
Jao et al.

[11] Patent Number: 5,166,145
[45] Date of Patent: Nov. 24, 1992

[54] ANTIEMETIC THERAPY

[75] Inventors: Francisco Jao, San Jose; Hoa I. Huynh, Fremont; Patrick S. L. Wong, Palo Alto, all of Calif.

[73] Assignee: Alza Corporation, Palo Alto, Calif.

[21] Appl. No.: 580,030

[22] Filed: Sep. 10, 1990

[51] Int. Cl.$^5$ ............................................. A61K 31/56
[52] U.S. Cl. ................................... 514/178; 514/179; 514/616; 514/454; 514/338; 514/180; 514/327; 514/872; 514/225.8; 514/171; 514/221; 514/226.2
[58] Field of Search ............... 424/473, 338, 221, 469, 424/454, 327; 514/616, 615, 178, 179, 180, 872, 225.8, 226.2

[56] References Cited
U.S. PATENT DOCUMENTS

| | | | |
|---|---|---|---|
| 2,799,241 | 7/1957 | Wurster | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,200,098 | 4/1980 | Ayer et al. | 128/260 |
| 4,285,987 | 8/1981 | Ayer et al. | 427/3 |
| 4,938,967 | 7/1990 | Newton | 424/469 |
| 5,032,578 | 7/1991 | Horovitz | 514/616 |

OTHER PUBLICATIONS

Rakel, R. E., Conn's Current Therapy, (1990), W. B. Sanders Co., Phila. Pa, pp. 6-11.

Primary Examiner—Thurman K. Page
Assistant Examiner—William E. Benston, Jr.
Attorney, Agent, or Firm—Paul L. Sabatine; Jacqueline S. Larson; Jean M. Duvall

[57] ABSTRACT

A dosage form is disclosed comprising an antiemetic and antinausea drug for treating vomiting and nausea.

2 Claims, 5 Drawing Sheets

ANTIEMETIC THERAPY

This invention pertains to antiemetic therapy. More particularly, the invention concerns a novel dosage form provided as an osmotic device comprising means for delivering an antiemetic drug at a controlled rate over time. The invention relates also to both a therapeutic composition comprising an antiemetic drug and to a method for treating emesis, which term as used herein includes nausea.

DESCRIPTION OF BACKGROUND ART

The emesis-nausea complex is one of the most frequent symptoms of disease. The emesis-nausea complex is induced often in a patient by chemo-therapeutic agents such as cisplatin, dacarbazine, dactinomycin, mechorethamine, and cyclophosphamide, by radiation therapy, in gastrointestinal carcinoma, during pregnancy, and as a result of certain types of motion in hypersensitive persons.

Drugs, such as antiemetics-antinauseants, are known in *Conn's Current Therapy*, pages 5 to 9, (1986), for treating emesis and nausea; however, there are serious disadvantages associated with their use. For example, these drug frequently are poorly soluble in aqueous fluids and accordingly they do not lend themselves for formulation into a drug delivery device. That is, the medical-dispensing art presently lacks a dosage form that can administer these drugs in a known amount per unit time for a predetermined length of time to produce the desired therapeutic effect.

In light of the above presentation, it will be appreciated by those versed in the dispensing art to which this invention pertains, that a pressing need exists for a dosage form that can deliver the valuable antiemetic-antinausea drugs to a patient in need of antiemetic-antinausea therapy. The pressing need exists also for an oral dosage form that can deliver these drugs at a controlled rate in a constant dose per unit time over a prolonged period of time for its beneficial effects. It will be appreciated further by those versed in the dispensing art that such a novel and unique dosage form that can administer an antiemetic-antinausea drug that is difficult to deliver, in a rate controlled dose over time, and simultaneously provide anti(emesis-nausea) therapy, would represent an advancement and a valuable contribution to the drug dispensing art.

DISCLOSURE OF OBJECTS OF THE INVENTION

Accordingly, in the light of the above presentation, it is an immediate object of this invention to provide a novel dosage form that overcomes the shortcomings of the prior art and fully satisfies the critical and unfilled need for the dosage form.

Another object of the invention is to provide a dosage form that can deliver difficult to deliver antiemetic-antinausea drugs thereby substantially fulfilling the pressing need of the prior art.

Another object of the invention is to deliver an antiemetic-antinausea drug from a dispensing system manufactured as a dispenser that is self-contained, self-starting, and self-powered in a fluid environment for dispensing said drug to an environment of use including humans.

Another object of the invention is to dispense a drug for treating an emesis-nausea complex from a dosage form comprising a wall that surrounds a lumen comprising the drug, a driving means for delivering the drug from the dosage form, and a rate controlled exit means for delivering the drug from the dosage form.

Another object of the present invention is to provide an antiemetic-antinausea drug in a dosage form useful for treating chemotherapy-induced emesis and nausea.

Another object of the present invention is to provide a dosage form comprising an antinausea-antiemetic drug for treating radiation induced emesis and nausea.

Another object of the present invention is to provide a dosage form comprising means for delivering an antiemetic drug for a prolonged period of time up to 12 hours, or for a prolonged period of time up to 24 hours, at a controlled rate and substantially-free of any premature dose dumping from the dosage form.

Another object of the present invention is to provide a composition comprising an antiemetic drug that can be dispensed from a dosage form over time.

Another object of the present invention is to provide a composition comprising an antiemetic drug in a dosage form that substantially reduces and/or substantially eliminates the unwanted influence of an environment of use on the dosage form and still provides controlled administration of the drug over time.

Another object of the invention is to provide an antiemetic drug on the exterior of a dosage form that is immediately released to provide instant antiemetic therapy to a patient in need of same.

Another object of the invention is to provide a method for treating emesis and nausea by administering to a patient suffering with same an antiemetic-antinausea drug at a controlled rate from a dosage form designed for delivering said drug.

Another object of the invention is to provide a complete therapeutic regimen from a composition comprising an antiemetic drug, and which composition can be dispensed from a dosage form, the use of which requires intervention only for initiation of therapy and possibly termination of the regimen.

Another object of the invention is to provide two doses of an antiemetic drug from a single dosage form to a patient in need of antiemetic therapy.

Other objects, features, and advantages of the invention will be more apparent to those versed in the dispensing art from the following specification, taken in conjunction with the drawing figures and the accompanying claims.

BRIEF DISCLOSURE OF THE DRAWING FIGURES

In the drawing figures, which are not drawn to scale, but are set forth to illustrate various embodiments of the invention, the drawing figures are as follows:

FIG. 2 is a view of the dosage form of FIG. 1, wherein FIG. 2 depicts a dose of an antiemetic-antinausea drug on the exterior surface for administering the antiemetic-antinausea drug instantly in a short period of time to a recipient;

In the drawing figures and in the specification, like parts in related figures are identified by like numbers. The terms appearing earlier in the specification, and in the description of the drawing figures, as well as embodiments thereof, are further described elsewhere in the disclosure.

DETAILED DESCRIPTION OF THE DRAWING FIGURES

Figure 1:
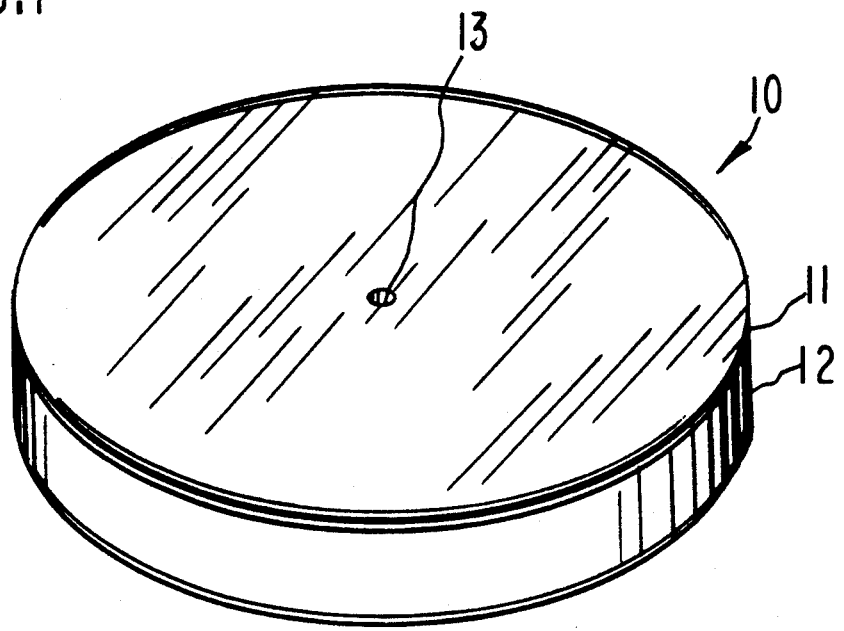
FIG. 1 is a view of a dosage form provided by the invention, which dosage form is designed, sized and adapted for admitting into a biological environment of use for delivering an antiemetic-antinausea drug.

Turning now to the drawing figures in detail, which drawing figures are an example of the dosage forms provided by the invention, and which examples are not to be construed as limiting, one example of the dosage form is illustrated in FIG. 1 and it is designed by the numeral 10. In FIG. 1, dosage form 10 comprises a body 11 comprising a wall 12 that surrounds and forms an internal compartment, not seen in FIG. 1. Dosage form 10 further comprises at least one exit means 13, or more than one exit means 13 for connecting the interior of dosage form 10 with exterior of dosage form 10.

Figure 2:
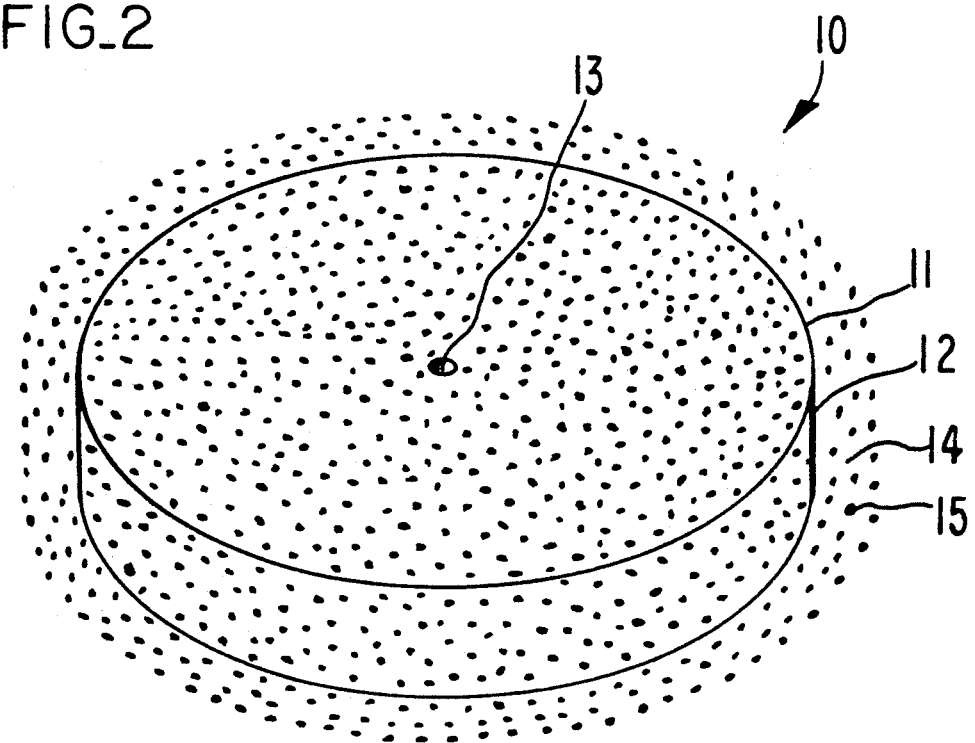

Dosage form 10, as seen in FIG. 2, depicts on presently preferred optional embodiment of the invention. In FIG. 2, dosage form 10 comprises body 11, wall 12 and exit means 13. Dosage form 10 in FIG. 2 also comprises an external coat 14 on the exterior surface of wall 12. Coat 14 is a therapeutic composition comprising 10 mg to 175 mg of an antiemetic-antinausea drug 15, represented by dots. Exterior coat 15 provides instant antiemetic-antinausea drug 15 for immediate therapy to a patient in need of antiemetic-antinausea therapy. The antiemetic-antinausea drug 15 is blended with an aqueous-soluble composition forming carrier such as methylcellulose, hydroxypropylcellulose, hydroxypropylmethylcellulose, blends of hydroxypropylcellulose and hydroxypropylmethylcellulose, optionally blended with a plasticizer such as polyethylene glycol or acetylated triglycerides or the like. Coat 14 provides instant antiemetic-antinausea therapy as coat 14 dissolves or undergoes dissolution in the presence of biological fluid and concurrently therewith delivers drug 15 to the drug receiving patient. Coat 14 comprising drug 15 provides instant antiemetic-antinausea therapy and it essentially overcomes the time required for drug 15 to be delivered from the interior of dosage form 10. A start-up time is needed for dosage form 10 to imbibe exterior fluid through wall 12 for dosage form 10 to hydrodynamically dispense drug through exit means 13.

Dosage form 10, as provided by this invention, and as seen in the above drawing figures can be manufactured for administering an antiemetic-antinausea drug by the oral route, and in another embodiment, dosage form 10 comprising exterior drug 15 can be sized and shaped for administering antiemetic-antinausea drugs by the sublingual and buccal routes. The sublingual and buccal routes can be used for quicker therapy and they can be used when a smaller dose of the drug is needed for therapy. The buccal and sublingual routes can be used as a by-pass of the first pass of hepatic metabolism of drug 15. The sublingual or buccal routes can be used for administering the first dose of drug, followed by permitting dosage form 10 to enter the stomach for subsequent drug delivery.

Figure 3:
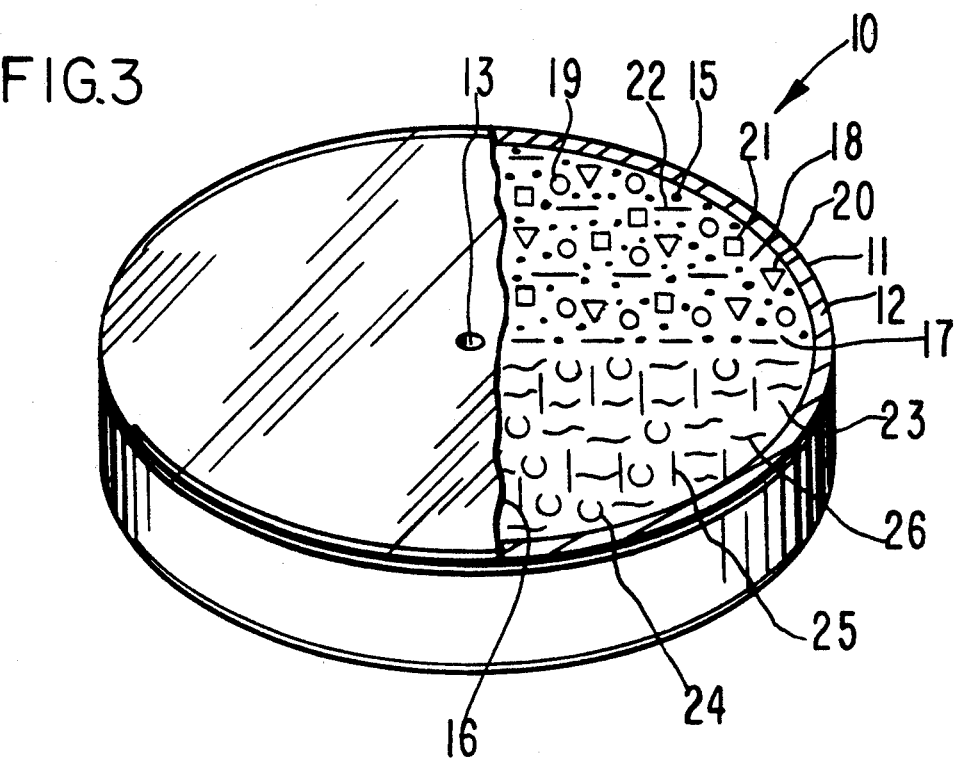
FIG. 3 is an opened view of FIG. 1 for illustrating the structure of the dosage form for delivering an antiemetic-antinausea drug over time.

In drawing FIG. 3, dosage form 10 is manufactured as an osmotic device, and it is seen in opened view at 16. In drawing FIG. 3, dosage form 10 comprises body 11, wall 12, that is sectioned at 16, and which wall 12 surrounds and delivers an internal compartment 17. Wall 12 comprises at least one exit means 13 that connects compartment 17 with the exterior of dosage form 10. Dosage form 10 can comprise more than one exit means 13, as presented later in the specification.

Wall 12 of dosage form 10, comprises totally, or in at least a part, a composition that is permeable to the passage of an exterior fluid present in the environment of use. Wall 12 is substantially impermeable to the passage of drug and other optional ingredients that may be present in compartment 17. The semipermeable wall 12 is substantially inert, that is, it maintains its physical and chemical integrity during the dispensing of a drug from dosage form 10. Wall 12 in a presently preferred embodiment comprises totally, or in at least a part, a nontoxic member selected from the group consisting of a cellulose ether, cellulose ester, cellulose ester-ether. The cellulosic polymers have a degree of substitution, D. S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D. S. up to 1 and an acetyl content up to 21%; cellulose acetate having an acetyl content of 32 to 39.8%; cellulose acetate having a D. S. of 1 to 2 and an acetyl content of 21 to 35%; cellulose acetate having a D. S. of 2 to 3 and an acetyl content of 35 to 44.8%, and the like. More specific cellulosic polymers include cellulose propionate having a D. S. of 1.8 and a propyl content of 39.2 to 45% and a hydroxyl content of 2.8 to 5.4%; cellulose acetate butyrate having a D. S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D. S. of 2.9 to 3 such as cellulose triacetate, cellulose trivalerate, cellulose trilaurate, cellulose tripalmitate, cellulose trisuccinate, and cellulose trioctanoate; cellulose diacylates having a D. S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional semipermeable wall forming polymers include acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selectively permeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked poly(vinylbenzyltrimethyl ammonium chloride). The polymers are known to the art in U.S. Pat. Nos. 3,845,770; 3916,899; and 4,160,020; and in *Handbook of Common Polymers* by Scott, J. R. and Roff, W. J., 1971, published by CRC Press, Cleveland, Ohio. In another embodiment, wall 12 of dosage form 10 of drawing FIG. 3 optionally comprises from 0 weight percent (wt %) to 30 wt % of a member selected from the group consisting of a cellulose ether selected from the group consisting of a hydroxypropylcellulose and a hydroxypropylmethylcellulose, and from 0 wt % to 30 wt % of a poly- ethylene glycol. The total weight of all components comprising wall 12 is equal to 100 wt %.

Dosage form 10, as seen in FIG. 3, comprises a therapeutically active antiemetic-antinausea drug layer 18. Drug layer 18 comprises at least one antiemetic-antinausea drug 15, depicted as dots, and in a presently preferred manufacture comprises 1 mg to 200 mg of ondansetron and its therapeutically active ondansetron derivatives including its salts and esters. The ondansetron drug 15 can be neat in layer 18, or it can be present in layer 18 optionally with 1 mg to 200 mg of at least one member selected from the antiemetic-antinausea group consisting of a-5HT antagonists for preventing vomiting and nausea associated with cancer therapy, radiation therapy and motion sickness, dronabinol, prochlorperazine, diphenhydramine, lorazepam, metoclopramide, dexamethasone, methylprednisolone, droperidol, chlorpromazine, and nabilone. The drug ondansetron is known in the *European Journal of Cancer and Clinical Oncology*, Volume 25, pages 515 to 519, (1989) and the drugs are disclosed in *The Merck Index*, Eleventh Edition (1989)

Drug layer 18 comprises also from 60 wt % to 80 wt % of a polyethylene oxide comprising an average 200,000 molecular weight identified by circles 19, from 5 wt % to 25 wt % of a polyethylene oxide comprising a 300,000 molecular weight identified by triangles 20, from 0 wt % to 25 wt % of a hydroxypropylmethylcellulose comprising a 9,000 to 140,000 average molecular weights and identified by squares 21, from 0 wt % to 3 wt % of a flow-promoting agent such as colloidal silicon dioxide, and from 0 wt % to 3 wt % of a surfactant, which tabletting excipients are represented by dashes 22. The total weight of all ingredients in drug layer 18 is equal to 100 wt %. The two different polyethylene oxide polymers 19 and 20 in drug layer 18 unexpectedly provides two advantages, first the two polymers serve as a carrier means for delivering a poorly soluble drug 15 from dosage form 10, and secondly, the two polymers substantially prevent a push layer from forming a channel through drug layer 18 towards exit means 13 thereby avoiding trapped pockets of drug 15 around exit means 13. The two polymers assure that essentially all of drug 15 will be delivered from dosage form 10.

Dosage form 10 comprises a second or push composition 23. The push composition 23 imbibes an aqueous fluid, such as a biological fluid or water through wall 12 into composition 23, causing it to expand against first composition 18 thereby causing the delivery of antiemetic-antinausea drug 15 through exit means 13. The second composition 23 comprises from 55 wt % to 85 wt % of a polyethylene oxide comprising a 5,000,000 to 7,500,000 molecular weight, represented by half circles 24, from 1 wt % to 20 wt % of a carboxyvinyl polymer comprising a 2,500,000 to 3,500,000 molecular weight illustrated by vertical lines 25, from 0 wt % to 40 wt % of an osmotically effective compound, which compounds are known also as osmotically effective solutes and osmagents and are identified by wavy line 26. The osmotic solutes 26 are heterogeneously or homogeneously mixed with the other ingredients comprising push layer 23 for imbibing an external fluid through wall 12 into push layer 23. Osmotically effective solutes useful for this purpose comprises magnesium sulfate, magnesium chloride, potassium sulfate, sodium sulfate, lithium sulfate, mannitol, urea, inositol, magnesium succinate, sodium chloride, potassium chloride, raffinose, sucrose, glucose, lactose and the like. Osmotic solutes and procedures for measuring the osmotic pressure are determined using a Model 320B, Vapor Pressure Osmometer, manufactured by the Hewlett Packard Co., Avondale, Pa, are disclosed by Wong et al in U.S. Pat. No. 4,765,989. Push composition 23 comprises also 0 wt % to 3 wt % of a colorant such as ferric oxide and from 0 wt % to 3 wt % of a lubricant such as magnesium stearate. The total weight percent of all ingredients in push composition 23 is equal to 100 wt %.

Figure 4:
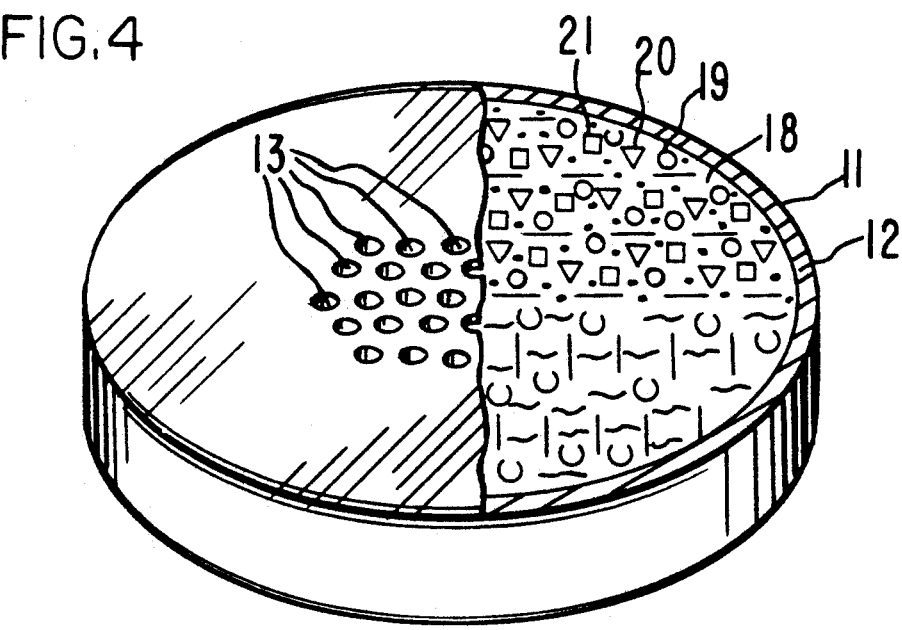
FIG. 4 depicts an opened view of the dosage form of FIG. 3, wherein the dosage form of FIG. 4 comprises a multiplicity of exit passageways for delivering an antiemetic-antinausea drug to a biological receptor; and, FIGS. 5 through 10 depict the release rate pattern over time and the cumulative amount of anti(emetic-nausea) delivered over time by the dosage form of the invention.

Dosage form 10, as seen in drawing FIG. 4, comprises at least one passageway 13, or more than one passageway 13. The expression "at least one passageway" includes aperture, orifice, bore, pore, porous element through which the drug can be pumped, diffuse, travel or migrate, hollow fiber, capillary tube, porous overlay, porous insert, microporous member, porous composition, and the like. The expression also includes a material that erodes or is leached from wall 12 in the fluid environment of use to produce at least one passageway in dosage form 10. Representative material suitable for forming at least one passageway, or a multiplicity of passageways, includes an erodible poly(-glycolic) acid or poly(lactic) acid member in the wall; a gelatinous filament; poly(vinyl alcohol); leachable materials such as fluid removable pore forming polysaccharides, salts, or oxides, and the like. A passageway or a plurality of passageways can be formed by leaching a material such as sorbitol, sucrose, lactose, fructose, or the like, from the wall. The passageway can have any shape such as round, triangular, square, elliptical, and the like, for assisting in the metered release of drug from dosage form 10. Dosage form 10 can be constructed with one or passageways in spaced apart relation on one or more than a single surface of a dosage form. Passageways and equipment for forming passages are disclosed in U.S. Pat. Nos. 3,845,770 and 3,916,899 by Theeuwes and Higuchi; in U.S. Pat. No. 4,063,064 by Saunders et al; and in U.S. Pat. No. 4,088,864 by Theeuwes et al. Osmotic passageways comprising controlled-drug releasing dimension, sized, shaped and adapted as a drug-releasing pore formed by aqueous leaching to provide a drug-releasing pore of controlled osmotic release rate are disclosed in U.S. Pat. No. 4,200,098 by Ayer and Theeuwes; and in U.S. Pat. No. 4,285,987 by Ayer and Theeuwes.

Wall 12 of osmotic dosage form 10 can be formed in one technique using the air suspension procedure. This procedure consists in suspending and tumbling the compressed drug-push laminate in a current of air and wall forming composition until a wall is applied to the drug-push compartment. The air suspension procedure is well-suited for independently forming the wall. The air suspension procedure is described in U.S. Pat. No. 2,799,241; *J. Am. Pharm. Assoc.*, Volume 48, pages 451 to 459, (1959); and ibid, Volume 49, pages 82 to 84, (196). Osmotic dosage forms can also be coated with a wall forming composition in a Wurster ® air suspension coater, using methylene dichloride-methanol cosolvent, 80:20, wt:wt, an ethanol-water, or acetone-water cosolvent, 95:5 wt:wt using 2.5 to 4% solids. The Aeromatic ® air suspension coater using a methylene dichloride-methanol cosolvent, 80:20 wt:wt, also can be used for applying the wall. Other wall forming techniques such as pan coating system, wall forming compositions are deposited by successive spraying of the composition on the drug-push compartment, accompanied by tumbling in a rotating pan. Finally, the wall coated compartments are dried in a forced air oven at 30° C. to 50° C. for up to a week to free dosage form 10 of solvent. Generally, the walls formed by these techniques have a thickness of 2 to 20 mils with a presently preferred thickness of 4 to 10 mils.

Dosage form 10 of the invention is manufactured by standard manufacturing techniques. For example, in one manufacture the beneficial drug and other ingredients comprising the drug layer facing the exit means are blended and pressed into a solid layer. The drug and other ingredients can be blended and pressed into a solid layer. The drug and other ingredients can be blended also with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer or push layer, is placed in contact with the drug layer. The osmopolymer-push layer is manufactured using techniques for providing the drug layer. The layering of the drug layer, and the osmopolymer-push layer can be fabricated by conventional press-layering techniques. Finally, the two-layer compartment forming members are surrounded and coated with an outer wall. A passageway is laser or mechanically drilled through the wall to contact the drug layer, with the dosage form optically oriented automatically by the laser equipment for forming the passageway on the preselected surface.

In another manufacture, the dosage form is manufactured by the wet granulation technique. In the wet granulation technique, for example, the drug and the ingredients comprising the drug layer are blended using an organic solvent, such as isopropyl alcohol-ethylene dichloride 80:20 v:v (volume:volume) as the granulation fluid. Other granulating fluid such as denatured alcohol 100% can be used for this purpose. The ingredients forming the drug layer are individually passed through a 40 mesh screen and then thoroughly blended in a mixer. Next, other ingredients comprising the drug layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through an 80 mesh screen and added to the dry screen granule blend. The granulation is put into milling jars and mixed on a jar mill for 1 to 15 minutes. The push layer is made by the same wet granulation techniques. The compositions are pressed into their individual layers in a Manesty ® press-layer press.

Another manufacturing process that can be used for providing the compartment-forming composition layers comprises blending the powdered ingredients for each layer independently in a fluid bed granulator. After the powdered ingredients are dry blended in the granulator, a granulating fluid, for example, poly(vinyl-pyrrolidone) in water, or in denatured alcohol, or in 95:5 ethyl alcohol /water, or in blends of ethanol and water is sprayed onto the powders. Optionally, the ingredients can be dissolved or suspended in the granulating fluid. The coated powders are then dried in a granulator. This process granulates all the ingredients present therein while adding the granulating fluid. After the granules are dried, a lubricant such as stearic acid or magnesium stearate is added to the granulator. The granules for each separate layer are pressed then in the manner described above.

The osmotic device of the invention is manufactured in another embodiment by mixing a drug with composition forming ingredients and pressing the composition into a solid lamina possessing dimensions that correspond to the internal dimensions of the compartment. In another embodiment the drug and other drug composition-forming ingredients and a solvent are mixed into a solid, or a semisolid, by conventional methods such as ballmilling, calendering, stirring or rollmilling, and then pressed into a preselected layer forming shape. Next, a layer of a composition comprising an osmopolymer and an optional osmagent are placed in contact with the layer comprising the drug. The layering of the first layering and the second layer comprising the osmopolymer and optional osmagent composition can be accomplished by using a conventional layer tablet press technique. The wall can be applied by molding, spraying or dipping the pressed shapes into wall forming materials. Another and presently preferred technique that can be used for applying the wall is the air suspension coating procedure. The procedure consists in suspending and tumbling the two layers in current of air until the wall forming composition surrounds the layers. The air suspension procedure is described in U.S. Pat. No. 2,799,241; *J. Am. Pharm. Assoc.*, Vol. 48, pp 451–459 (1979); and, ibid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1979, (1970), published by Mack Publishing Co., Easton, Pa.

Exemplary solvents suitable for manufacturing the wall, the laminates and laminae include inert inorganic and organic solvents final laminated wall. The solvents broadly include members selected for the group consisting of aqueous solvents, alcohols, ketones, esters, ethers, aliphatic hydrocarbons, halogenated solvents, cycliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane ethylene glycol monoethyl ether, ethylene glycol monoethyl acetate, methylene dichloride, ethylene dichloride, propylene dichloride, carbon tetrachloride, chloroform, nitroethane, nitropropane, tetrachoroethan, ethyl ether, isopropyl ether, cyclohexane, cyclooctane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

EXAMPLE 1

A dosage form adapted, designed and shaped as an oral osmotic delivery system is manufactured as follows: first, 150 g of ondansetron, a 5-hydroxytryptamine antagonist useful for the management of emesis, 717.5 g of polyethylene oxide comprising 200,000 molecular weight, 100 g of polyethylene oxide comprising a 300,000 molecular weight, and 30 g of hydroxypropylmethylcellulose comprising a 9,600 molecular weight, are individually screened by forcing them through a 40 mesh screen. Then, all the freshly screened ingredients are transferred to a commercial blender and blended for 15 minutes to yield a homogenous mass. Next, 500 ml of denatured alcohol is added to the blender and the ingredients blended for 20 minutes to produce a wet granulation. Next, the wet granulation is passed through a 20 mesh stainless steel screen to yield granules. The granules are spread on a tray and placed in a 40° C. oven to dry for 24 hours. The dried granules are passed through a 20 mesh stainless steel screen and 2.44 g of the lubricant magnesium stearate added to the granules. The granules-lubricant mixture is transferred to a blender and the ingredients homogeneously blended for 5 minutes. The total weight of the granulation is 946.6 g and it comprises 15 wt % ondansetron, 71.75 wt % polyethylene oxide possessing a 200,000 molecular weight, 10 wt % polyethylene oxide possessing a 300,000 molecular weight, 3 wt % hydroxypropylmethylcellulose comprising a 9,600 molecular weight, and 0.25% magnesium stearate.

An osmotic, expandable push layer for delivering the ondansetron drug from the delivery system is prepared as follows: first, 1375.5 g of a polyethylene oxide having a 5,000,000 molecular weight, 401 g of the osmagent sodium chloride, 100 g of hydroxypropylmethylcellulose having a 11,300 molecular weight and 100 g of a carboxyvinyl polymer having a 3,000,000 molecular weight, and 20 g of ferric oxide are individually screened through a 40 mesh screen and then transferred to a mixer. The mixer is run at low speed for 15 minutes to yield a homogeneous blend. Next, 200 ml of ethanol is added to the mixer and the mixing continued for an additional 15 minutes to produce a homogeneous wet granulation. The wet granules are screen through a 20 mesh screen and spread on trays for air drying for 16 hours. The dried granules are passed through a 20 mesh stainless steel screen and 4.9 g of magnesium stearate is added thereto and blended to produce lubricated granules. The total weight of the osmotic granulation is 1368.4 g and it comprises 68.75 wt % of the polyethylene oxide polymer of 5,000,000 molecular weight, 20 wt % of sodium chloride, 5 wt % of the hydroxypropylmethylcellulose, 5 wt % of the carboxyvinyl polymer, 1 wt % of ferric oxide and 0.25 wt % of magnesium stearate.

Next, the ondansetron drug composition and the osmotic push composition are brought into laminating arrangement in a two-layered press. The press comprised a 5/16 inch round die, to which is added 110 mg of the ondansetron composition and 83 mg of the osmotic composition. The two compositions are compressed together under 3 tons compression pressure to yield the two compositions in bilaminated arrangement.

Next, the bilaminate is surrounded with a semipermeable wall. The wall-forming composition is prepared as follows: first, 5787 ml (95 wt %) of acetone is blended with 240 ml (5 wt %) of purified water to produce a cosolvent. Then, 190 g of cellulose acetate comprising an acetyl content of 39.8% and 10 g of polyethylene glycol are blended together and added to the cosolvent to yield a coating solution comprising 4 wt % solids. The wall-forming composition is sprayed onto and around the bilaminate in Freund Model HCT-30 Hi-Coater (pan coater). The coated wall surrounding the laminate weighed 11.32 mg.

Figure 5:
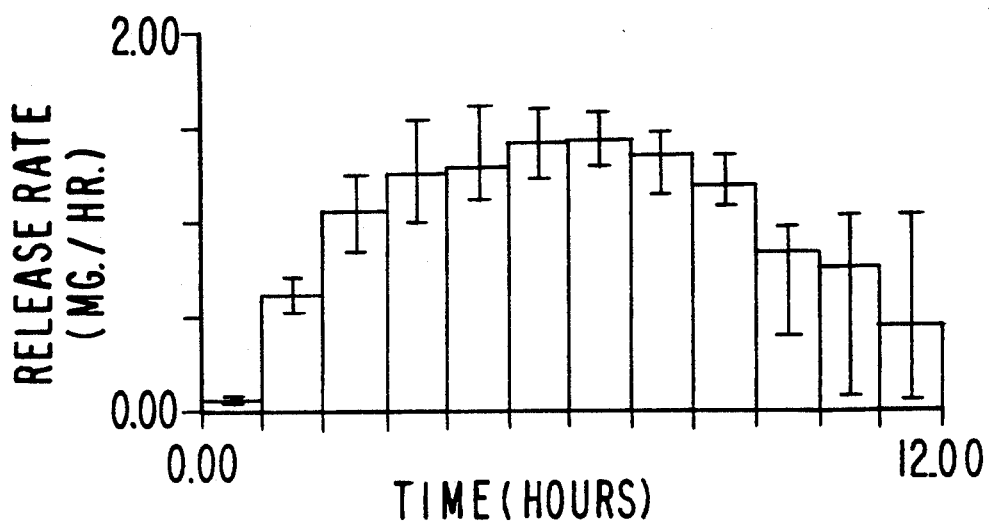
Figure 6:
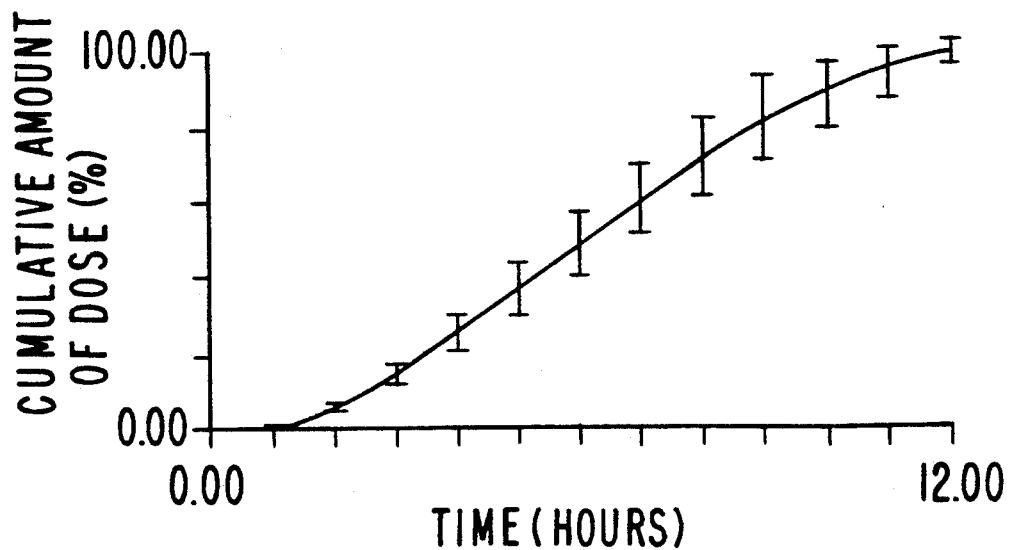

Next, two 25 mil exit ports are drilled on the drug surface of the dosage form for delivering the drug to a recipient. Finally, the coated and drilled systems are dried for 48 hours in an oven at 45° C. to evaporate the cosolvent. The final osmotic dosage form comprises 13.2 ng of ondansetron representing a 10% over dose for administering 12 mg of ondansetron to the drug recipient. Accompanying FIG. 5 depicts the release rate over time and accompanying FIG. 6 depict the cumulative amount of ondansetron released over 12 hours.

EXAMPLE 2

Figure 7:
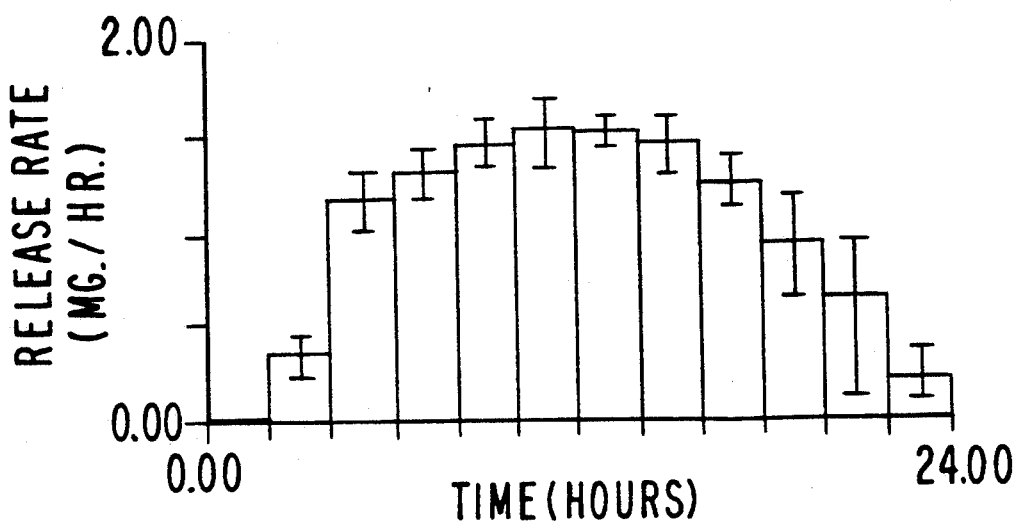
Figure 8:
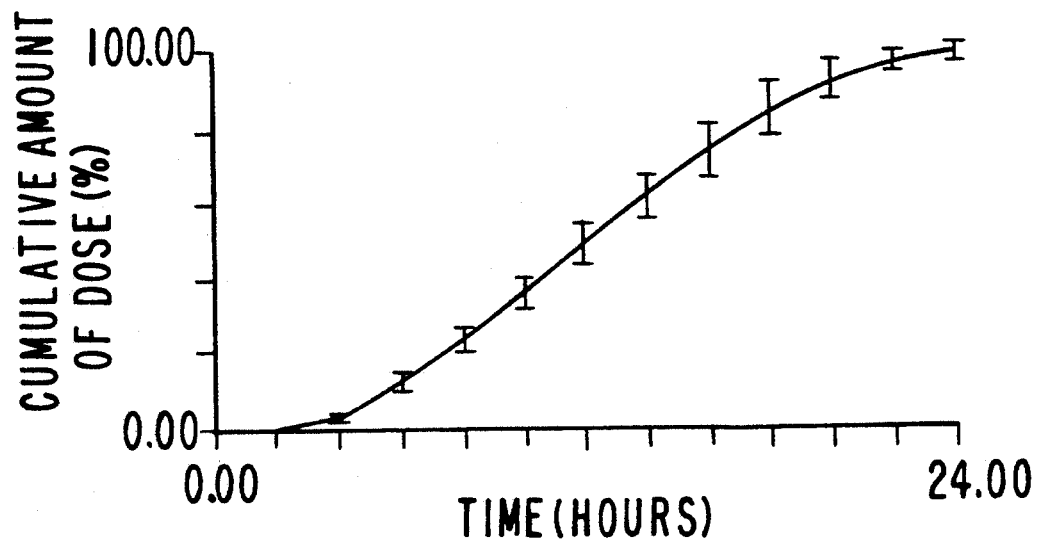

Following the procedure of Example 1, an osmotic device is manufactured with all conditions as described except that the ondansetron drug layer weighed 220 mg and comprised 15 wt % ondansetron hydrochloride, 71.75 wt % polyethylene oxide comprising a 200,000 molecular weight, 3 wt % hydroxypropylmethylcellulose comprising a 9,600 molecular weight, 10 wt % polyethylene oxide comprising a 300,000 molecular weight and 0.25 wt % magnesium stearate. The osmotic device comprises 26.4 mg of drug, a 10% overage for administering 24 mg of drug. The device exhibits a mean release rate of 1.387 mg/hr. Accompanying FIG. 7 depicts the release rate over 24 hours and FIG. 8 depicts the cumulative amount of ondansetron released over 24 hours.

EXAMPLE 3

Figure 9:
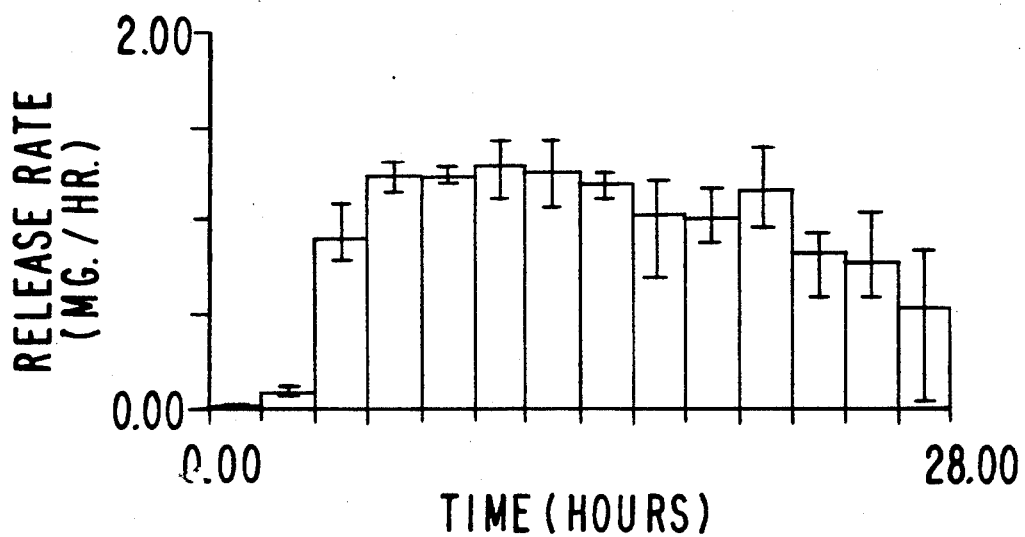
Figure 10:
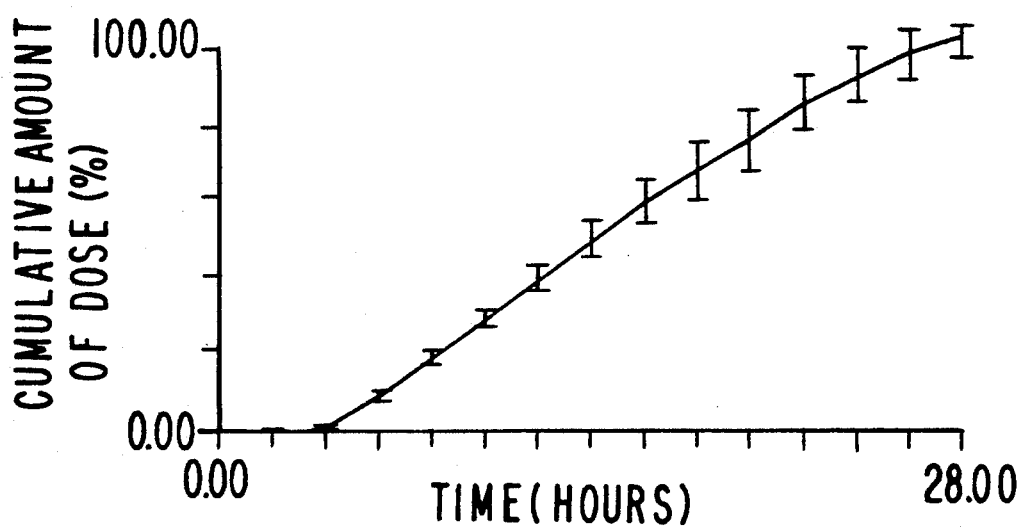

Following the procedures of Examples 1 and 2, an osmotic dosage form is prepared comprising 24 mg of ondansetron which is released at a rate of 1.244 mg/hr. Accompanying FIG. 9 depicts the release rate over 28 hours and accompanying FIG. 10 depicts the cumulative amount of ondansetron released over 28 hours.

EXAMPLE 4

An antiemetic-antinausea composition comprising from 4 mg to 50 mg of the antiemetic-antinausea drug metoclopramide is prepared for dispensing from the dosage form of Example 1. The composition is prepared by blending and compressing the two drugs with the composition forming ingredients of Example 1.

EXAMPLE 5

An antiemetic composition is prepared comprising from 1 mg to 50 mg of ondansetron and from 1 mg to 50 mg of a member selected from the group consisting of a benzamine, butyrophenone, phenothiazine, corticosteroid, benzodrazipine and cannabinoid by blending the combination and compressing the combination with the pharmaceutically acceptable carrier of Example 1 for dispensing the combination from the dosage form provided by the invention.

EXAMPLE 6

The antiemetic composition is described in Example 5, wherein the benzamine is metoclopramide, the butyrophenone is haloperidol or droperidol, the phenothrazine is prochlorperazine or chlorpromazine, the corticosteroid is dexamethasone or methylprednisolone, the benzodrazipine is lorazepam, and the cannabinoid is nabilone or dronabinol.

DESCRIPTION OF METHOD OF PERFORMING THE INVENTION

A presently preferred embodiment of the invention pertains to a method for delivering an antiemetic-antinausea drug to the gastrointestinal tract of a human in need of antiemetic-antinausea therapy, wherein the method comprises the steps of: (A) admitting orally into the gastrointestinal tract of the human a dosage form comprising: (1) a non-toxic wall composition comprising means for imbibing an external aqueous fluid through the wall into the dosage form, which wall surrounds and defines; (2) an internal compartment; (3) an antiemetic-antinausea drug composition in the compartment comprising a dosage unit amount of said drug; (4) a push composition in the compartment for pushing the antiemetic-antinausea drug from the compartment; (5) at least one exit means in the wall for delivering the drug from the dosage form; (B) imbibing fluid through the wall into the compartment thereby causing the antiemetic-antinausea composition to form a deliverable dosage form and concomitantly causing the push composition to expand and push the drug through the exit means from the dosage form; and (C) deliver the therapeutic drug in a therapeutically effective amount at a controlled rate over a prolonged period of time to the patient in need of said therapy. The method also comprising dispensing a dose amount of said drug from an instant release exterior dosage amount of drug to the patient for providing instant antiemetic-antinausea therapy.

Inasmuch as the foregoing specification comprises preferred embodiments of the invention, it is understood that variations and modifications may be made herein, in accordance with the inventive principles disclosed, without departing from the scope of the invention.

We claim:

1. A composition comprising from 1 mg to 200 mg of an ondansetron and from 1 mg to 200 mg of at least one member selected from the group consisting of a benzamine, butyrophenone, phenothiazine, corticosteroid, benzodrazipine and a cannabionoid, said composition therapeutically indicated for treating vomiting and nausea when provided as a dosage form.

2. A composition comprising from 1 mg to 200 mg of an ondansetron; from 1 to 200 mg of at least one member selected from the group consisting of metoclopramide, haloperidol, droperidol, prochlorperazine, chlorpromazine, dexamethasone, methylprednisolone, lorazepam, nabilone and dronabinol; and a pharmaceutically acceptable carrier; and wherein the total weight of all ingredients in the composition is equal to 100 wt % and the composition is indicated for lessening vomiting and nausea in a patient when administered as a dosage form.

* * * * *